(12) United States Patent
Qian et al.

(10) Patent No.: US 8,048,411 B2
(45) Date of Patent: Nov. 1, 2011

(54) CO-TRANSPLANTATION OF HEPATIC STELLATE CELLS AND ISLET CELLS

(75) Inventors: Shiguang Qian, Broadview Heights, OH (US); Lina Lu, Broadview Heights, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 988 days.

(21) Appl. No.: 11/840,633

(22) Filed: Aug. 17, 2007

(65) Prior Publication Data
US 2008/0145342 A1      Jun. 19, 2008

Related U.S. Application Data

(60) Provisional application No. 60/838,406, filed on Aug. 17, 2006.

(51) Int. Cl.
*C12N 5/00* (2006.01)
(52) U.S. Cl. ....... 424/93.7; 424/562; 435/366; 435/370; 435/374; 435/382
(58) Field of Classification Search ................ None
See application file for complete search history.

(56) References Cited

U.S. PATENT DOCUMENTS

| 7,211,600 B2 * | 5/2007 | Lipson et ..................... 514/418 |
| 7,402,567 B2 * | 7/2008 | Chojkier et al. ............. 514/18.9 |
| 2005/0288353 A1 * | 12/2005 | Lipson et al. ................ 514/414 |

* cited by examiner

*Primary Examiner* — Blaine Lankford, Jr.
(74) *Attorney, Agent, or Firm* — Tarolli, Sundheim, Covell & Tummino LLP

(57) ABSTRACT

A method of inhibiting graft rejection includes isolating Hepatic Stellate Cells from a mammal liver, activating the isolated Hepatic Stellate Cells, and administering a combination of Hepatic Stellate cells and a graft to a mammal.

10 Claims, 14 Drawing Sheets x100 x100

Insulin (green) and CD31 (red) day 14

Insulin (green), α-SMA (red), nuclear (blue)

CO-TRANSPLANTATION OF HEPATIC STELLATE CELLS AND ISLET CELLS

RELATED APPLICATION

This application claims priority from U.S. Provisional Patent Application Ser. No. 60/838,406, filed Aug. 17, 2006, the subject matter of which is incorporated herein by reference.

This invention was made with government support under Grant No. NIH Grant DK58316 awarded by National Institute of Health. The government has certain rights in the invention.

TECHNICAL FIELD

The present invention relates to a method of transplanting cells and particularly relates to a method of transplanting cells using Hepatic Stellate cells.

BACKGROUND OF THE INVENTION

Certain chronic diseases destroy the functional cells in affected organs. Mammals with such diseases are often unable to produce proteins or hormones necessary to maintain homeostasis and usually require numerous exogenous substances to survive. Transplanting healthy organs or cells into a mammal suffering from such a disease may be necessary to save the mammal's life. This type of therapy is generally regarded as a last alternative to curing an otherwise fatal condition. Such transplants, however, are often rejected by the body due to an immune response initiated in response to the foreign tissue or cells. Presently, the only recourse to combat this immune response is to administer chronic non-specific immunosuppression agents. Unfortunately, this only trades the complications of one chronic disease with other complications caused by the immunosuppression agent.

One disease which scientists have attempted to treat with organ and/or cellular transplants but have had very limited success is diabetes mellitus. Diabetes mellitus is a prevalent degenerative disease in mammals. It is characterized by a relative or complete lack of insulin secretion by the beta cells within the islets of Langerhans of the pancreas or by defective insulin receptors.

This insulin deficiency prevents normal regulation of blood glucose levels and often leads to hyperglycemia and ketoacidosis. When administered to a mammal, insulin promotes glucose utilization, protein synthesis, formation and storage of neutral lipids and the growth of certain cell types.

SUMMARY OF THE INVENTION

The present invention relates to a method of treating a disease that results from a deficiency of a biological factor in a mammal. The method includes administering Hepatic Stellate cells and a therapeutically effective amount of graft cells that produce the biological factor to a mammal in need of such treatment. The Hepatic Stellate cells are administered in an amount effective to prevent graft rejection.

Another embodiment of the present invention describes a method of preventing graft rejection. The method includes isolating Hepatic Stellate cells from a mammal liver, activating the isolated Hepatic Stellate cells, and administering a combination of the Hepatic Stellate cells and a graft into a mammal.

In yet another embodiment, the present invention describes a method of treating diabetes mellitus in a mammal. The method includes isolating Hepatic Stellate cells from a mammal liver, activating the isolated Hepatic Stellate cells, and then administering a therapeutically effective amount of a combination of Hepatic Stellate cells and pancreatic islet of Langerhans cells into a diabetic mammal.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1A:
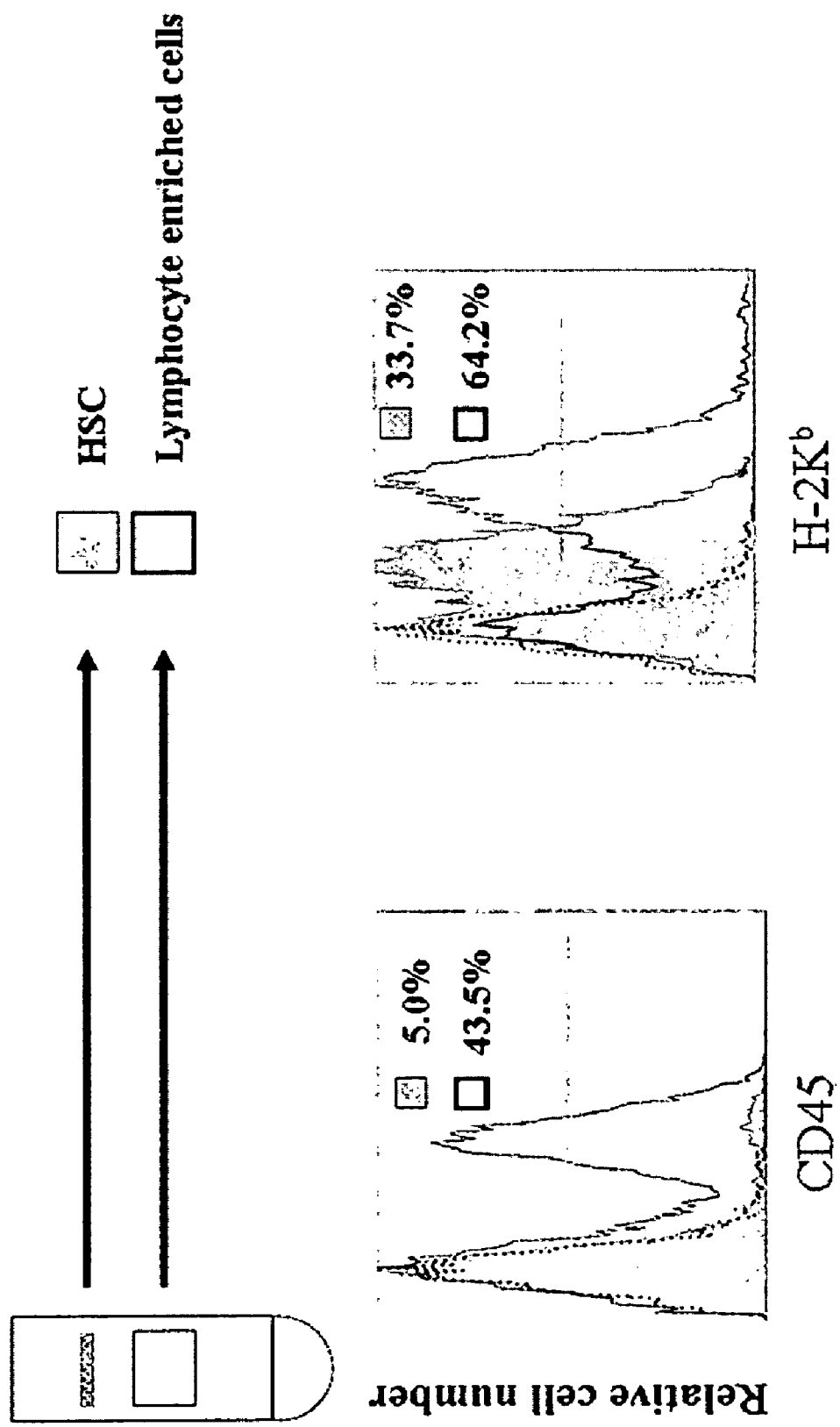
FIG. 1 illustrates HSC isolation and activation. (A) HSCs were isolated from B6 mouse liver non-parenchymal cells by gradient centrifugation as described in the Methods. Flow cytometric analyses (histograms) showed that freshly isolated HSCs (filled) were distinct from hepatic lymphocytes (opened) in not expressing CD45 (lymphocyte marker) and MHC class II. ($IA^d$). Open dotted areas are isotype controls. (B) HSCs were cultured in an uncoated plastic for 2 [quiescent (qHSCs)] or 7 days [activated (aHSCs)]. Irradiated HSCs (50 Gy) were added at the beginning into an MLR culture in which splenic T cells ($2\times10^5$) from B6 ($H2^b$) mice and irradiated (20 Gy) BALB/c ($H2^d$) DCs (B6 DCs and HSCs only were used as controls) were cultured at a T:DC:HSC ratio of 40:2:1 for 3 days. Compared with the MLR culture without HSCs, T cell thymidine up taking stimulated by allogeneic DCs were almost completely inhibited by activated HSCs. ($p<0.05$), but not by quiescent HSCs ($p>0.05$).

The present invention relates to a method of preventing or inhibiting graft rejection. The method includes isolating Hepatic Stellate cells from a mammal liver, activating the isolated Hepatic Stellate cells, and administering a combination of the Hepatic Stellate cells and a graft to a mammal. In one embodiment, the mammal is a human. In another embodiment the Hepatic Stellate cells are immunologically compatible to the mammal recipient. In a further embodiment, the combination of Hepatic Stellate cells and a graft are administered to a mammal for the treatment of diabetes mellitus.

In an aspect of the invention, the Hepatic Stellate cells and a graft are administered to the subject by implantation. The graft may include an autograft, an allograft, and a xenograft. The term autograft as used in the present invention describes the transfer of tissues or cells within the same mammal. Allografts, as used in the present invention, describe the transfer of tissues or cells between two genetically dissimilar mammals of the same species. The term xenograft in the present invention describes the transfer of tissues or cells between two mammals of different species.

In another aspect of the invention, the combination of Hepatic Stellate cells and a graft may comprise a mixture of Hepatic Stellate cells and graft cells. Alternatively, the combination of Hepatic Stellate cells and graft cells can be in the form of a pellet. The pellet can include a plurality of Hepatic Stellate cells that are provided about a plurality of graft cells. The pellet can be formed by centrifuging the Hepatic Stellate cells and graft cells. The Hepatic Stellate cells can be provided as a multiple layered capsule or coating surrounding the graft.

The Hepatic Stellate cells may be isolated from mammal liver non-parenchymal cells. In one embodiment, the isolated Hepatic Stellate cells are activated to express an immune regulatory molecule, such as B7H1. The Hepatic Stellate cells can be activated by culturing the Hepatic Stellate cells in a culture media for an amount of time. The culture media can include, for example, RPMI-1640 supplemented with about 10% fetal calf serum and about 10% horse serum. The Hepatic Stellate cells can be cultured in a cell culture flask at a density of about $10^5$/ml.

The amount of time the Hepatic Stellate cells are cultured to activate the cells is at least about 5 days, for example, between about 5 days and about 10 days. In an aspect of the invention, the amount of time the Hepatic Stellate cells are cultured to activate the cells is about 7 days.

The combination of Hepatic Stellate cells and graft may be administered using any technique capable of introducing the combination into the mammal. Such techniques can include, for example, through a catheter, subcutaneous injection, or through a small incision in the mammal's abdomen.

In one embodiment, the combination of Hepatic Stellate cells and graft are administered to the mammal's liver. The combination may also be administered by injection into the mammal's renal subscapular space or, more specifically, under the subscapular space on the medial aspect of the mammal's kidney.

An immunosuppressive agent can be administered to the mammal to further suppress rejection of the transplanted graft. Examples of immunosuppressive agents or anti-rejection drugs that can be administered to the mammal include dacliximab, sirolimus, tacrolimus and cyclosporine.

In another aspect of the invention, the graft can include pancreatic islets of Langerhans. The islets are made up of two types of cells: alpha cells, which make glucagons, a hormone that raises the level of glucose in the blood, and beta cells, which make insulin. The islets of Langerhans cells may be isolated from the pancreas by conventional methods such as collagenase V digestion. In an aspect of the present invention the graft comprise of alpha cells from islet of Langerhans clusters. The graft may also include beta cells from islet of Langerhans clusters.

The amount of graft cells included in the combination can be a therapeutically effective amount to treat a disorder and/or repair a defect in the mammal. The amount of Hepatic Stellate cells included in the combination can be an mount effective to prevent or inhibit rejection of the graft in the mammal. The amount of Hepatic Stellate cells included in the combination is dependent upon the amount of graft cells in the combination. For example, where islet of Langerhans cells are administered in a therapeutically effective amount of at least about 200 islets at least about $1 \times 10^4$ Hepatic Stellate cells can be included in the combination to present rejection.

The present invention also relates to a method of treating a disease that results from a deficiency of a biological factor in a mammal. The method includes administering a combination of Hepatic Stellate cells and a therapeutically effective amount of cells that produce the biological factor to a mammal in need of such treatment. The Hepatic Stellate cells in the combination are administered in an amount effective to prevent rejection of the cells, which produce the biological factor.

The biological factor can be a protein or non-protein compound that is necessary for cellular metabolism and homeostasis. In one aspect, the biological factor can be a hormone. In another aspect, the biological factor can be insulin and the disease can be diabetes mellitus. In a further aspect, the cells that produce the biological factor are pancreatic islet of Langerhans cells.

The factor producing cells are provided by transforming suitable host cells with a nucleic acid capable of expressing the factor of interest. Transformed cells are provided by methods known to one of ordinary skill in the art, and can be found in a myriad of textbooks and laboratory manuals, including Sambrook et al. (1989) Molecular Cloning: A Laboratory Manual, Cold Spring Harbor Laboratories, Cold Spring, N.Y.

In yet another embodiment the method includes administering a therapeutically effective amount of exogenous biological factor following the transplantation of the cells that produce the biological factor.

The present invention further relates to a method of treating diabetes mellitus in a mammal including isolating Hepatic Stellate cells from a mammal liver, activating the isolated Hepatic Stellate cells, and administering a therapeutically effective amount of a combination of Hepatic Stellate cells and pancreatic islet of Langerhans cells into a diabetic mammal. In an embodiment of the present invention, the method may be used to treat Type 1 or Type 2 diabetes mellitus.

The combination of Hepatic Stellate cells and a pancreatic islet of Langerhans cells may be composed of a mixture. The combination of Hepatic Stellate cells and a pancreatic islet of Langerhans cells may alternatively be combined in a pellet. The combination may also form a multiple layered capsule or coating surrounding the pancreatic islet of Langerhans cells.

The Hepatic Stellate cells may be isolated from mammal liver non-parenchymal cells. In an embodiment the isolated Hepatic Stellate cells are activated to express an immune regulatory molecule. The immune regulatory molecule can be B7H1.

A preferred cell culture media is composed of RPMI-1640 supplemented with 10% fetal calf serum and 10% horse serum and cultured in a cell culture flask at a density of $10^5$/ml.

EXAMPLE 1

Materials and Methods

Animals

Male C57BL/6 (B6; H2"), C3H(H2$^k$), BALB/c (H2$^d$), B10.BR(H2$^k$) and EGFP transgenic mice [C57BL/6-TgN (ACTbEGFP) 10sb, H2$^b$] were purchased from the Jackson Laboratory (Bar Harbor, Me.). B6. B7-H-1 KO mice were kindly provided by Dr. Lieping Chen at Johns Hopkins University Medical School, Baltimore, Mass. All animals were maintained in the specific pathogen-free facility of the University of Pittsburgh Medical Center (Pittsburgh, Pa.) and provided with Purina rodent chow (Ralston Purina, St. Louis, Mo.) and tap water ad libitum and used at 8-10 weeks of age following the guidelines (NIH publication 86-23 revised 1985).

Preparation of HSCs

HSCs were isolated from mouse liver nonparenchymal cells (NPC) as previously described in Freidman et al. N Engl J Med 328:1828-1835 (1993), with some modifications, see Yu et al., Hepatology 40:1312-1321 (2004). The isolated HSCs were cultured at a density of $10^5$/ml in cell culture flask (25 cm² surface area) (Nunclon™, Roskilde, Denmark) with RPMI-1640 (Mediatech Inc., Hendon, Va.) supplemented with 10% fetal calf serum and 10% horse serum in a 5% $CO_2$ in air at 37° C. for 2 (quiescent) or 7 days (activated). Cell viability at all times was greater than 90% as determined by trypan blue exclusion. The purity of HSCs was determined by desmin immunostaining and the typical light microscopic appearance of the lipid droplets, see Liu et al., J Biol Chem 278:11721-11728 (2003). HSCs used in this study were cultured on flask for 7 days for activation, unless otherwise was described.

Flow Cytometry

Expression of HSC surface molecules was determined by flow cytometric analysis, using an EPICS ELITE flow cytometer (Coulter Corporation, Hialeah, Fla.). Cells were stained with the mAbs against CD45 (rat 1 $gG_{2b}$) or CD54 (hamster IgG). MHC class I and II antigens were detected with mAbs against $H2K^b$ and $1A^b$ (both mouse $IgG_{2a}$), respectively (all from RD. PharMingen, San Diego, Calif.). Expression of B7-H1 was identified by anti-B7-H1 specific mAb (rat $IgG_{2a}$, eBioscience, San Diego, Calif.). The appropriate isotype control antibodies were used in the experiments.

Dendritic Cell (DC) Culture

As previously described in Lu et al., Transplantation 60:1539-1545 (1995), bone marrow cells were isolated from mouse femurs and tibias, and, after lysis of red blood cells, cultured in RPMI-1640 complete medium in the presence of mouse recombinant (r) GM-CSF (4 ng/ml) and IL-4 (1000 unit/ml) (both from Schering-Plough, Kenilworth, N.J.). Non-adherent cells were released spontaneously from the proliferating cell clusters. These cells were then harvested, washed and resuspended in medium.

Mixed Lymphocyte Reaction (MLR)

Nylon wool-eluted B6 spleen T cells (2×$10^5$/well in 100 µl) were cultured in triplicate in 96-well round-bottom microculture plates (Corning, Corning, N.Y.) with graded doses of γ-irradiated (20Gy; X-ray source) DCs from BALB/c mice in RPM1-1640 complete medium, for 3-4 days in 5% $CO_2$ in air. [³H]TdR (1 µCi/well) was added for the final 18 hr, and incorporation of [³H]TdR into DNA was assessed by liquid scintillation counting. Results were expressed as mean c.p.m.±1S.D. To examine the effect of HSCs on T cell proliferation, γ-irradiated (50Gy) HSCs were added into the cultures at the beginning of the culture.

In Vitro CTL Assay

B6 spleen T cells cultured with γ-irradiated (20Gy) BALB/c DCs at a ratio of 10:1 for 5-6 days were used as effectors. P815 ($H2^d$), EL4 ($H2^b$) or R1.1 ($H2^k$) lymphoma cell lines (4×$10^6$, all from American Type Culture Collection, Rockville, Md.) labeled with 100 µCi $Na_2{}^{51}CrO_4$ (NEN, Boston, Mass.) were used as donor-specific, syngeneic or third party targets, respectively. They were plated at 5×$10^3$ cells/well in 96-well round-bottom culture plates (Corning). Serial, two-fold dilutions of effector cells were added (total volume of 200l/well). The percentage of $^{51}Cr$ release was determined after incubating the plates for 4 hr at 37° C. in RPMI-1640 complete medium in 5% $CO_2$ in air. An aliquot (100 µl) of supernatant was recovered from each well after centrifugation at 300 g for 1 mm. Maximum $^{51}Cr$ release was determined by lysis of the target cells.

In Vivo CTL Assay

In vivo CTL activity against islet donor-specific targets was assessed as described in Barchet et al, Eur J Immunol 30:1356-1363 (2000) with some modification. Briefly, BALB/c mouse splenocytes $10^7$/ml) were labeled with a low concentration (0.5 µM) of CFSE (Molecular Probes, Eugene, Oreg., $CFSE^{low}$) and used as donor targets. B6 splenocytes labeled with a high concentration (5 µM) of CFSE ($CFSE^{high}$) were used as a syngeneic control. Ten million cells of each population were mixed, and adjusted to 50:50 ratio, and i.v. injected into naïve B6 mice (controls) or B6 recipients of islets (BALB/c) alone or islet (BALB/c) plus HCSs (B6). Three hours later, mice were bled. The number of $CFSE^{low}$ and $CFSE^{high}$ cells in spleen was analyzed by flow cytometry. 100,000 events were collected and analyzed using the ModFit LT cell cycle analysis software (Verity Software House, Topsham. ME). Percent specific lysis of fluorescent BALB/c spleen cells in each mouse is calculated as: 100-[(percentage $CFSE^{high}$/percentage $CFSE^{low}$)×100].

Islet Transplantation

Islets were isolated from donor pancreas by collagenase V (Sigma Aldrich) digestion as previously described in Gotoh et al., Transplantation 40:437-438 (1985) with slight modification, see Alexander et al., Diabetes 51:356-365 (2002). After separation on a Ficoll gradient (Type 400, Sigma Aldrich), the islets were purified by hand picking. Diabetic mice were induced by an intra-peritoneal injection of streptozotocin (220 mg/kg body weight, Sigma Aldrich). Only these mice with non-fasting blood glucose levels exceeding 350 mg/dl were used as recipients. 300 freshly isolated islets alone or mixed with 1 or 3×$10^5$ HSCs were aspirated into polyethylene tubing (PE-50, Becton Dickinson, Parsippany, N.J.), and pelleted by centrifugation for 2 min, and then gently placed under the subcapsular space on the medial (hilar) aspect of the kidney of isoflurane-anesthetized recipients. Transplantation was considered successful if the non-fasting blood glucose returned to and remained normal (<150 mg/dl) for the first 4 days post-transplantation. After transplantation, tail vein non-fasting blood glucose was monitored every 2 days following transplantation, and the first day of two consecutive readings of blood glucose >350 mg/dl was defined the date of diabetes onset. No immunosuppressive reagents were administered throughout the experiments.

Immunohistochemistry

CD4, CD8 T cells, and HSCs in the cryostat sections were identified by biotinylated rat anti-mouse CD4, CD8 (B. D. PharMingen) and mouse anti-mouse a smooth muscle actin (SMA) mAb ($IgG_{2a}$, Sigma Aldrich), respectively. The isotype and species-matched irrelevant mAbs were used as controls. The apoptotic cells were identified by terminal deoxynucleotidyl transferase-mediated dUTP nick end labeling (TUNEL). Each experiment was performed with a negative control (without dUTP) and a positive control (10-min pretreatment of slides with 1 mg/ml DNase in reaction buffer). The color was developed by an enzyme reaction using avidin-biotin-alkaline phosphatase complex (ABC) as the substrate. The slides were counterstained with Harris' hematoxylin and mounted with Crystal mount (Biomeda Corp., Foster City, Calif.). For quantification, the staining positive cells were counted under a microscopy, and a total of 30 high power fields (hpf) were randomly selected in each group. The immunofluorescence protocols were performed to determine expression of CD3, CD31(both from BD Pharmingen), insulin (Santa Cruz Biotechnology, Santa Cruz, Calif.), αSMA (Sigma Aldrich) and EGFP (Abeam, Cambridge, Mass.).

Slides were analyzed using an Olympus BX 51 fluorescence microscope (Olympus America). Quantification of CD31, insulin, and CD3 was performed using MetaMorph software.

Statistical Analysis

The parametric data are presented as mean±1 SD and statistical significance was determined by Student's t test (two-tailed). Graft survival between groups of transplanted animals was compared using the log-rank test. Values of p<0.05 were considered statistically significant.

Results

Isolation and Activation of HSCs

Figure 1B:
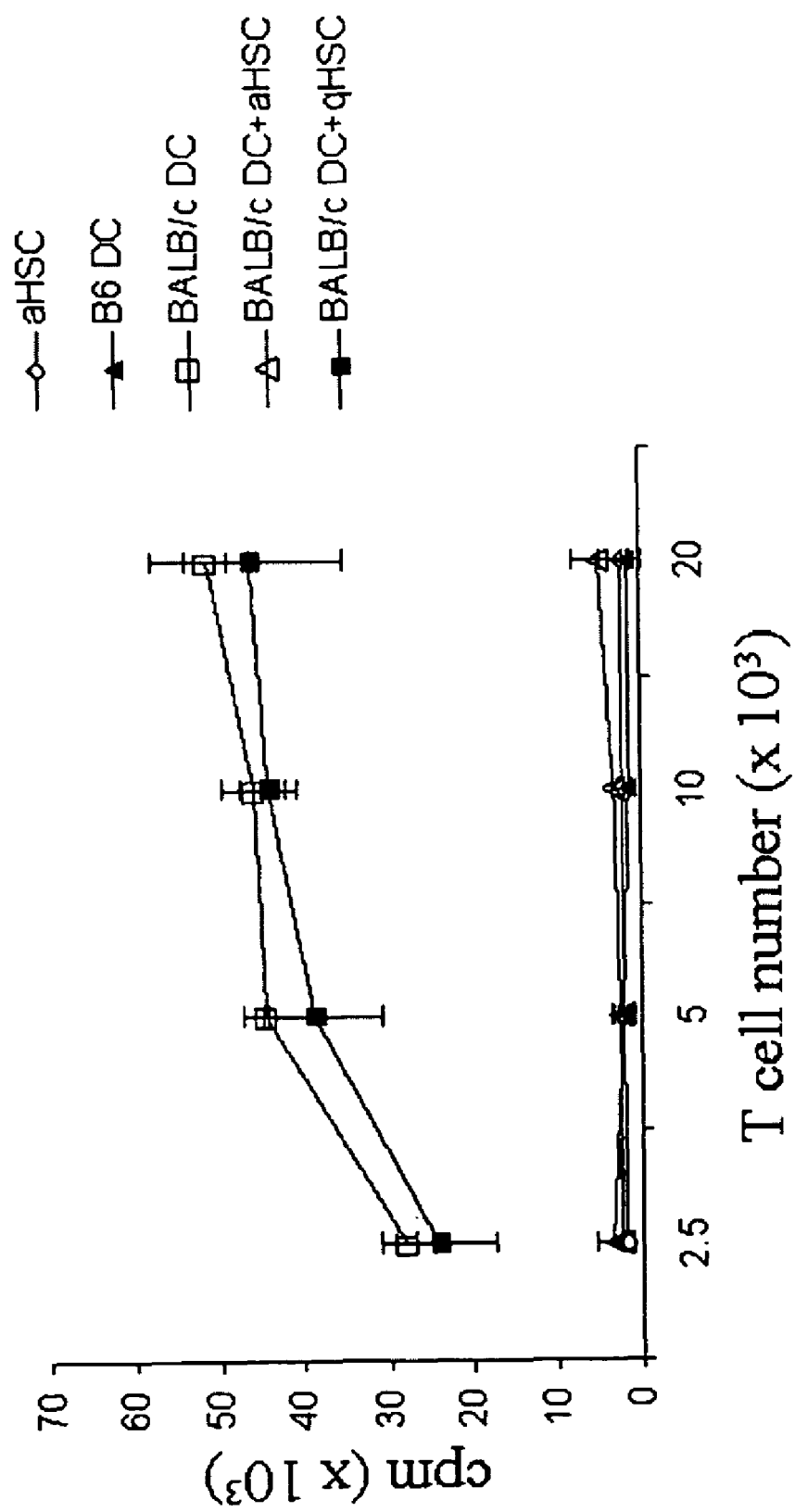

HSCs were isolated from B6 mouse Liver NPC with purity >95% determined by desmin immunostaining expressed MHC class 1, but not CD45 (FIG. 1A). HSCs were activated by culture for 7 days, and the activation status was determined by positive staining of αSMA, B7-H1, and 1CAM-1 as previous described. The immune inhibitory function of activated HSCs was examined by addition of HSCs in a MLR assay. FIG. 1B showed that activated HSCs markedly inhibited T cell thymidine uptake, but not the quiescent HSCs.

Co-Transplantation with HSCs Protects Islet Allografts from Rejection

Figure 2A:
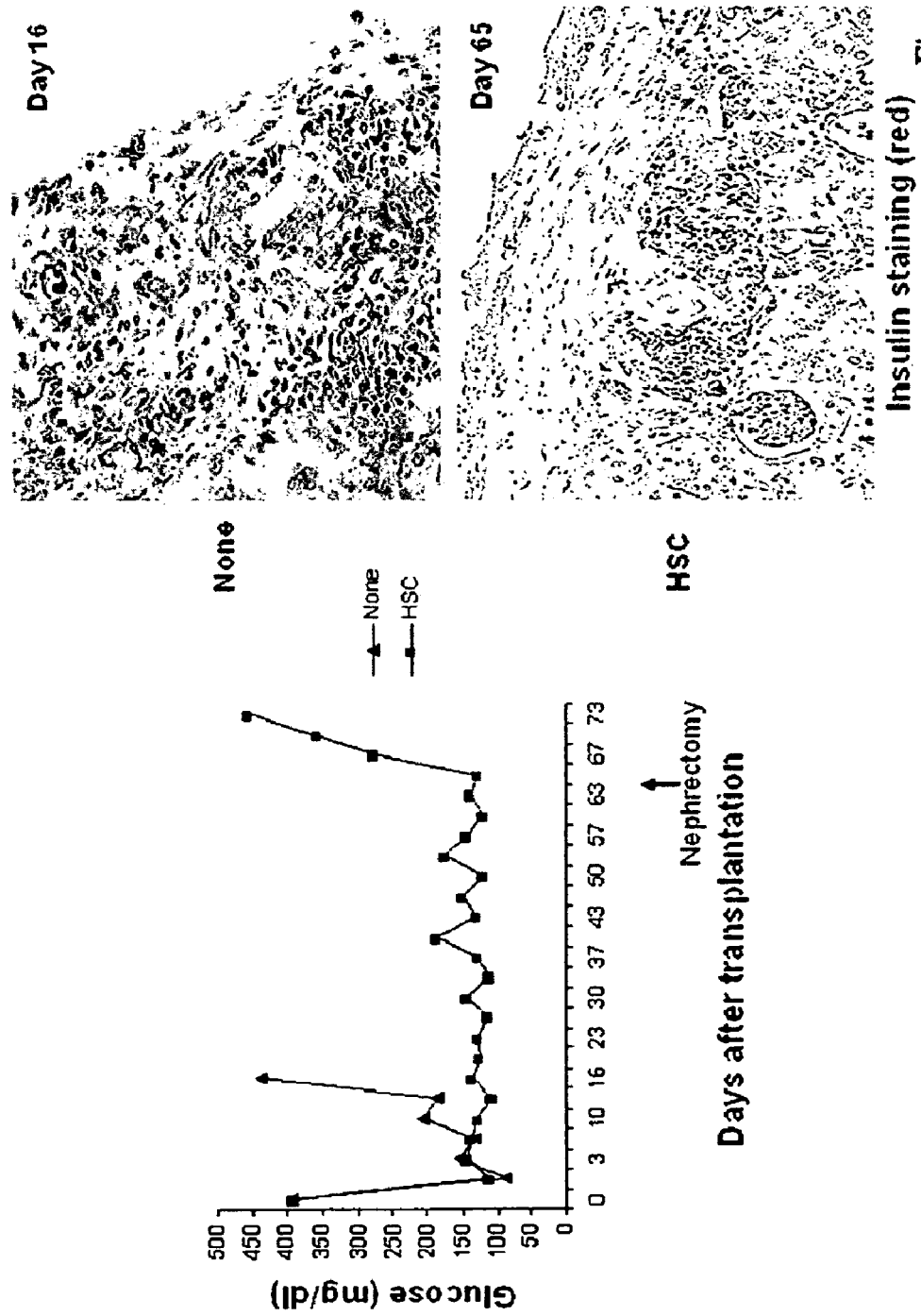
FIG. 2 illustrates co-transplantation with HSCs provides a local protection of islet allografts. (A) Blood glucose levels in chemically-induced diabetic B6 mice were shown before (day 0) and after transplantation of 300 BALA/c islets alone under the left renal capsule (-▲-). The islet graft destruction was indicated by recurrence of hyperglycemia on day 15 post transplant, and very few insulin positive islets with massive infiltrates were seen in histochemical examination (right upper). In contrast, after transplantation of 300 BALB/c islets plus $3\times10^5$ B6 HSCs under the left renal capsule (-■-), euglycemia was maintained until left kidney was removed on day 65 post-transplant. Immunochemistry showed the presence of numerous insulin positive islets under the renal capsule (right lower). (B) Co-transplant with HSCs did not affect in vivo specific CTL activity. BALB/c mouse splenocytes ($10^6$) labeled with low CFSE (0.5 µM, used as donor-specific targets) were mixed with same number of B6 splenocytes labeled with high CFSE (5 µM, used as internal controls). Both $CFSE^{low}$ and $CFSE^{high}$ cell populations were clearly identified by flow cytometry. The mixed cells were then injected i.v. into normal B6 mice (none) or B6 recipients that had been transplanted with islets (BALB/c) alone or islet (BALB/c) plus HCSs (B6) under the left renal capsule for 12 days. The incidence of $CFSE^{low}$ and $CFSE^{high}$ cells in spleen was determined by flow cytometry at 3 h after injection. Target lysis was calculated based on the incidence of $CFSE^{low}$ and $CFSE^{high}$ cells as described in the Methods. CTL against BALB/c targets in normal B6 mice was 62.5%. Transplant with islet allografts alone enhanced the specific CTL to 82%. Co-transplant with HSCs had no effect on this CTL activity (80.6%). (C) To determine whether co-transplanted HSCs exerted remote effect on islet allografts transplanted in the opposite side kidney, diabetic B6 recipients received 300 BALB/c islets plus $3\times10^5$ B6 HSCs under the left renal capsule, and 300 BALB/s islets alone under the right renal capsule. Animals were sacrificed on day 18 following transplantation. The graft sections were immunostained by anti-insulin mAb (red). All data are representative of three separate experiments.

To examine the immune inhibitory activity of HSCs in vivo, we examined the effect of co-transplant with HSCs on survival of islet allografts. HSCs of B6 ($H2^b$) mice were mixed with 300 islets of BALB/c ($H2^d$) pancreata, and transplanted under the capsule of the left kidney of diabetic B6 recipients. Co-transplantation with activated (cultured for 7 days), but not quiescent (cultured for 2 days) HSCs ($3 \times 10^5$) markedly prolonged islet allograft survival (median survival time [MST]>60 days, compared with grafts of islets alone (MST=1 3 days, p<0.01). 55% (6 of 11) of recipients that received islets plus activated HSCs remained euglycemia for more than 60 days, whereas none (0 of 9) of recipients with islet-only grafts remained euglycemia by 17 days after transplantation (Table 1). Removal of the kidney bearing the islet grafts was performed in all animals maintaining euglycemia for more than 60 days at various times (from day 65 to 170 post-transplant), resulting in a prompt return to hyperglycemia (FIG. 2A), indicating the functional transplanted islets. This was supported by immunohistochemical staining showing that the removed kidney contained healthy insulin positive islets (FIG. 2A). The required number of activated HSCs were $3 \times 10^5$ since the MST of islets plus $1 \times 10^5$ HSCs was only 18 days (Table 1, p>0.05 compared with islet alone group). In addition, HSCs need to be syngeneic to the recipient since co-transplant with BALB/c (allogeneic) or C3H($H2^K$, third party) HSCs slightly, but not statistically significantly, prolonged survival of islet allografts (Table 1, both p>0.05 compared with islet alone group). To rule out the possibility that this protective activity of HSCs was specific to B6 strain, the similar experiments were performed in other strain mice including BALB/c and B10.BR($H2^k$). HSCs showed similar protective effect on the co-transplanted islet allografts.

Co-Transplanted HSCs do not Confer a Systemic Immune Suppressive Effect.

Figure 2B:
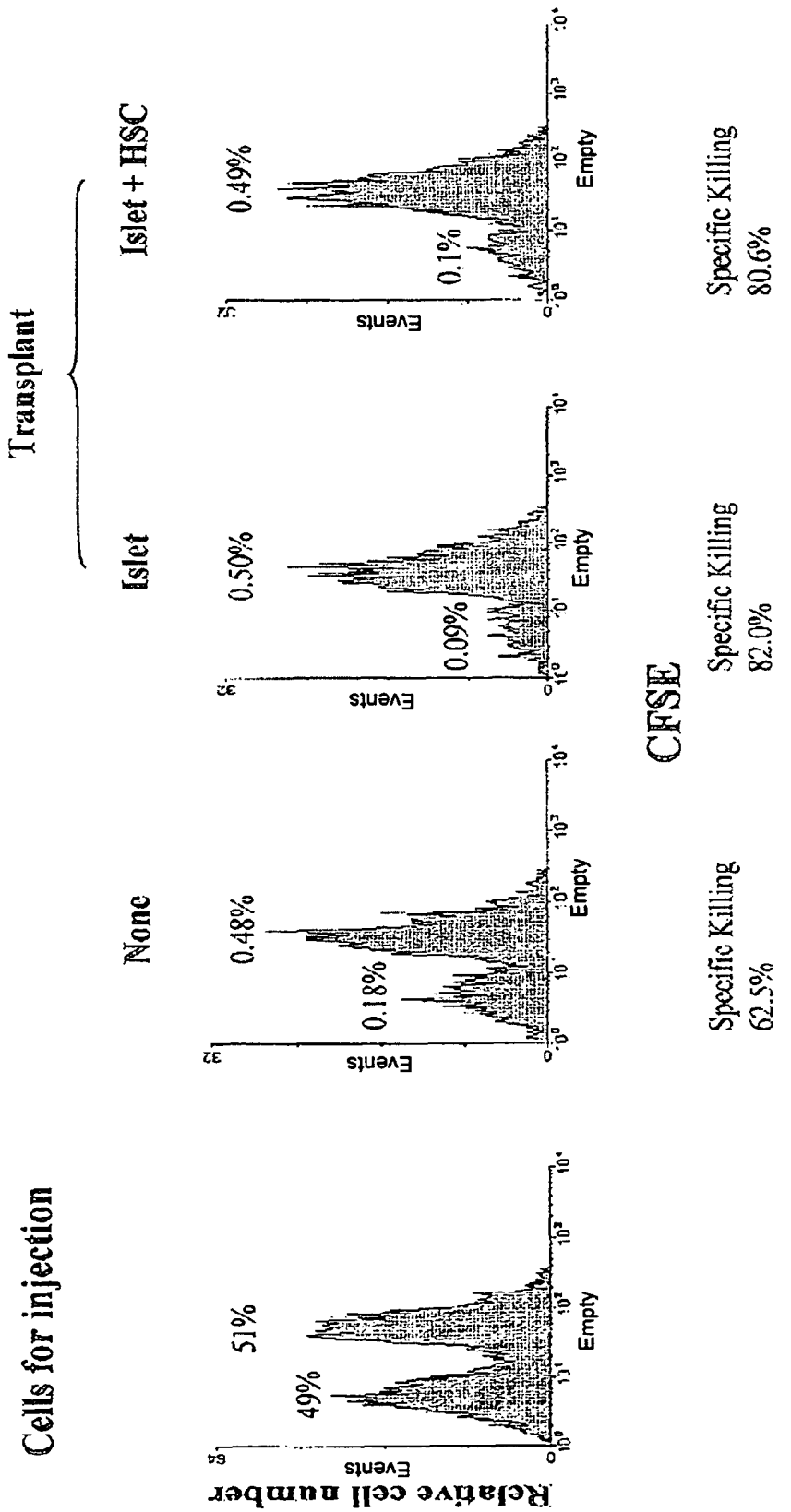
Figure 2C:
Figure 2C:
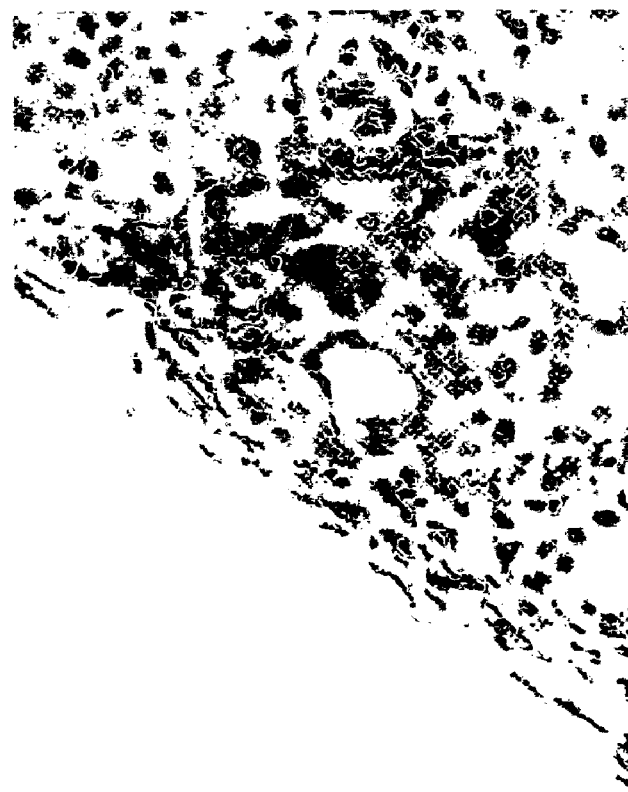

To distinguish between local vs. systemic immunosuppressive effect of HSCs, we examined the impact of co-transplanted HSCs on in vivo specific CTL activity against donor (BALB/c) targets. BALB/c splenocytes labeled with low CFSE (donor targets) were mixed with same number of B6 splenocytes labeled with high CFSE (syngeneic control targets), and then injected into normal B6 (control) and B6 recipients that had transplanted with BALB/c islet alone or plus HCSs (B6) for 12 days. The number of $CFSE^{low}$ and $CFS^{high}$ cells in recipient mouse spleen was measured by flow cytometry 3 h after injection. The specific lysis of donor targets was calculated based on the numbers of $CFSE^{low}$ and $CFSE^{high}$ cells. CTL against BALB/c targets in normal B6 mice was 62.5% (FIG. 2B), reflecting an allogeneic CTL activity in normal recipients. Transplant with islet allografts alone enhanced the specific CTL to 82%. Co-transplant with HSCs did not alter allogeneic CTL activity (80.6%) (FIG. 2B), suggesting lack of systemic immunosuppressive effect. This was supported by the fact that HSCs transplanted into the right kidney failed to protect islet allografts in left kidney (Table 1 group 6, p>0.05 compared with group 1). To exclude the possibility that transplanted syngeneic HSCs lacking persistent stimulation by infiltrating lymphocytes became dysfunctional, we performed the following experiments (n=3). HSCs were mixed with allogeneic (BALB/c) islets and transplanted into left kidney, while additional 300 islets without HSCs were transplanted into right kidney. The animals were sacrificed at day 18 post transplantation for graft histological and insulin staining. In all three animals, HSCs showed protection of islets that were transplanted together in left kidney, while very few functional islets were seen in right kidney (FIG. 2C). To determine status of donor-specific tolerance, skin grafts from BALB/c or C3H (third party strain) were transplanted onto three normal B6 or B6 recipients whose islet allografts (BALB/c) were survived for more than 100 days. Survival of BALB/c skin grafts on B6 recipients accepting BALB/c islet grafts was not significantly prolonged compared with controls (data not shown), indicating an absence of specific tolerance.

TABLE 1

Effect of Co-transplantation With HSCs on Survival of BALB/c Islet Allografts in B6 Recipients

| Group | HSC | Number ($\times 10^5$) | Islet Graft Survivial (days) | $MST_a$ (days) |
|---|---|---|---|---|
| 1 | None[b] | — | 9 (×2), 10, 12, 13, 15, 16 (×2), 17 | 13 |
| 2 | B6[c] | 3.0 | 10, 11 (×3), 13, 15, 16 (×2), 18, 20 | 14 |
| 3 | B6[d] | 1.0 | 10, 12, 16 (×2), 18 (×2), 21, 24, 28 | 18 |
| 4 | B6[d] | 3.0 | 30, 35, 48 (×2), 50, 65[e], 77 (×2)[e], 100[e], 122[e] 170[e] >60 | |
| 5 | BALB/c[d] | 3.0 | 12, 14, 21 (×3), 23, 24, 26, 30, 36 | 22 |
| 6 | C3H[d] | 3.0 | 13, 15, 20, 26 (×2) | 20 |
| 7 | B6[d,f] | 3.0 | 10, 11, 12, 13, 18 | 12 |
| 8 | B6, B7-h1 KO[d] | 3.0 | 16, 17, 26, 26, 37 | 26 |

[a]MST, median survival time.
[b]Islets (BALB/c) allografts alone were transplanted under the renal capsule of left kidney of B6 recipients.
[c]and dHSCs were cultured for 2 days[c] or 7 days[d], then mixed with islet allografts, and co-transplanted under the renal capsule of left kidney of B6 recipients.
[e]Euglycemia maintained for more than 60 days posttransplantation, and the animals were killed on the indicated day for further studies.
[f]HSCs were implanted under the renal capsule of the opposite side (right) kidney.

Co-Transplanted HSCs form a Multiple-Layered Capsule Surrounding the Islets.

Figure 3A:
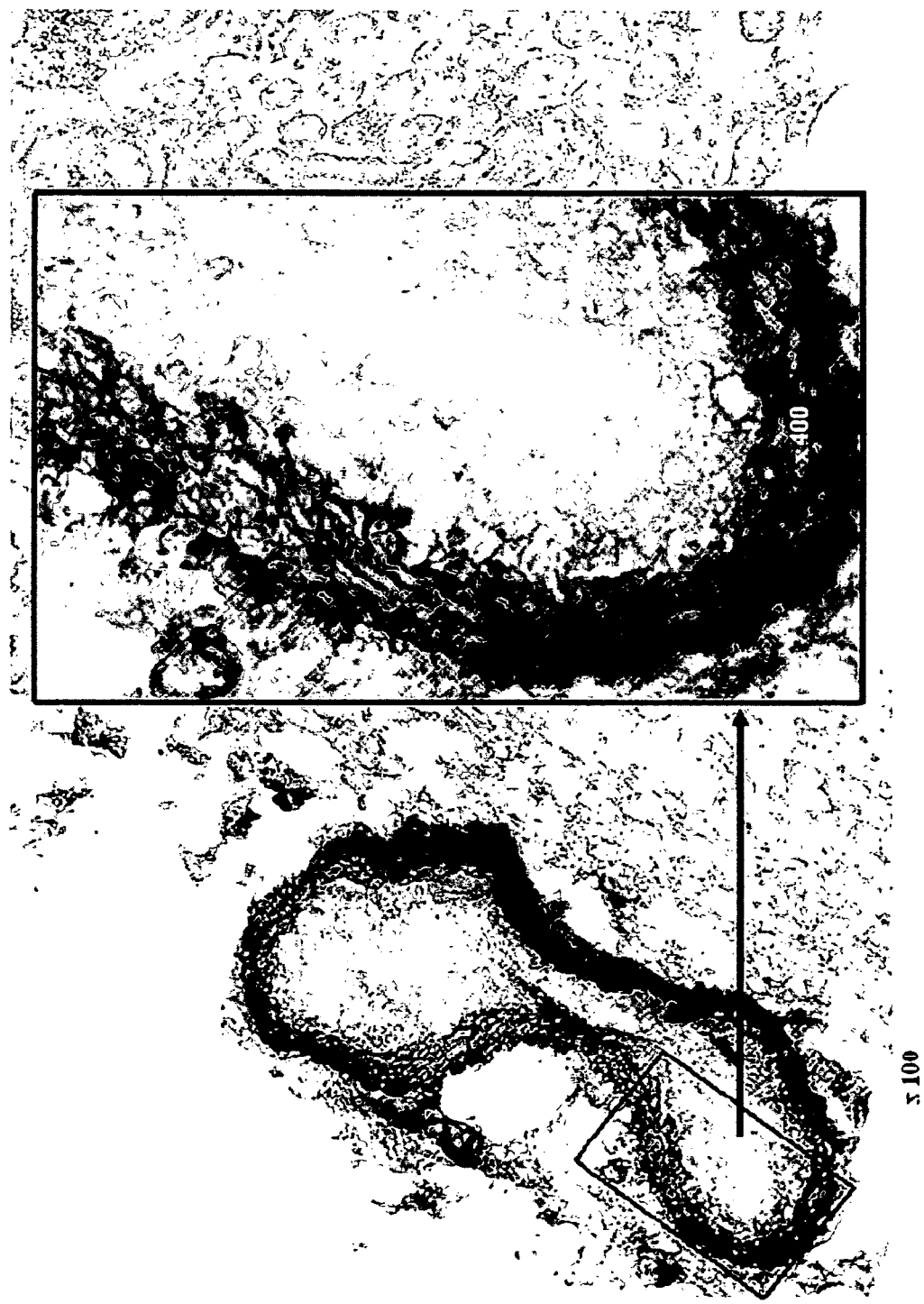
FIG. 3 illustrates formation of an αSMA positive capsular rim surrounding islets following islet plus HSCs co-transplantation. Chemically-induced diabetic B6 recipients were co-transplanted with 300 BALB/c islets plus $3 \times 10^5$ B6 HSCs under left renal capsule and maintained normal blood glucose levels. (A) The animal was sacrificed on day 122 post-transplant. The cryostat sections of the left kidney were stained with anti-SMA mAb. A complete multiple layered SMA positive capsule was formed surrounding the islets which were healthy in morphology. (B) The animal was sacrificed on day 100 following transplantation. The cryosections of the left kidney were stained with fluorescence-labeled anti-αSMA (green) and insulin (red). The nuclei were stained blue. To examine the role of co-transplanted HSCs in formation of the capsule surrounding the islets. Chemically-induced diabetic B6 recipients were transplanted with 300 BALB/c islets plus $3 \times 10^5$ B6 HSCs from EGFP transgenic mice (B6 background) under left renal capsule. Animals were sacrificed on day 21 and 100. (C)HSCs from EGFP transgenic mice were examined under fluorescent microscopy showing green fluorescence. (D) The cryostat sections of the grafts from an animal sacrificed on day 21 post-transplant were examined under a fluorescent microscopy showing a ring structure of fluorescent (green) cells, suggesting formation of capsular rim by co-transplanted HSCs. (E) The cryostat sections of the grafts from an animal sacrificed on day 100 post-transplant were stained with anti-GFP (green), anti-insulin (red) and Hoescht for nuclei (blue), and examined under fluorescent microscopy. The picture indicated the close approximation of co-transplanted HSCs with the islet allografts. The data are representative of three separate experiments.

To determine how HSCs provide a local protective effect, the long-term survived islet grafts were harvested for immunohistochemical examinations. Interestingly, the transplanted islet allografts were surrounded by a multi-layered capsule, which was stained positive for αSMA (FIG. 3A). α-SMA is one of the six actin isoforms in mammalian tissue and is considered to be typical for vascular smooth muscle cells, see Skalli et al., J Cell Biol. 103:2787-2796 (1986). It is the most reliable marker for myofobroblast cells, and widely used as an important marker for activated HSCs during liver injury, see Serini et al., Exp Cell Res 250:273-283 (1999).

Figure 3B:
Figure 3C:
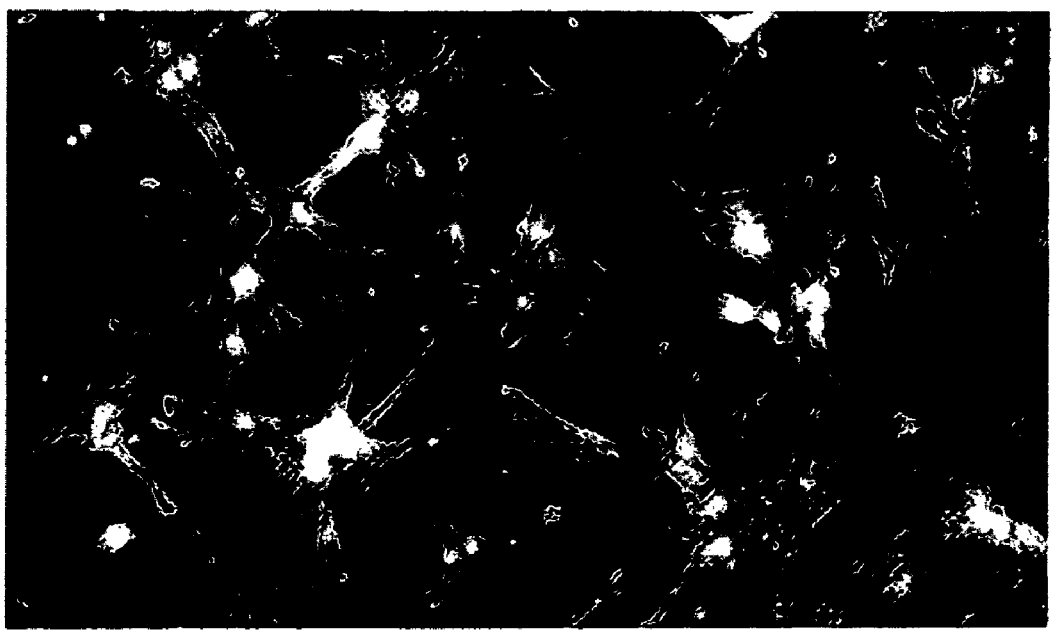
Figure 3D:
Figure 3E:
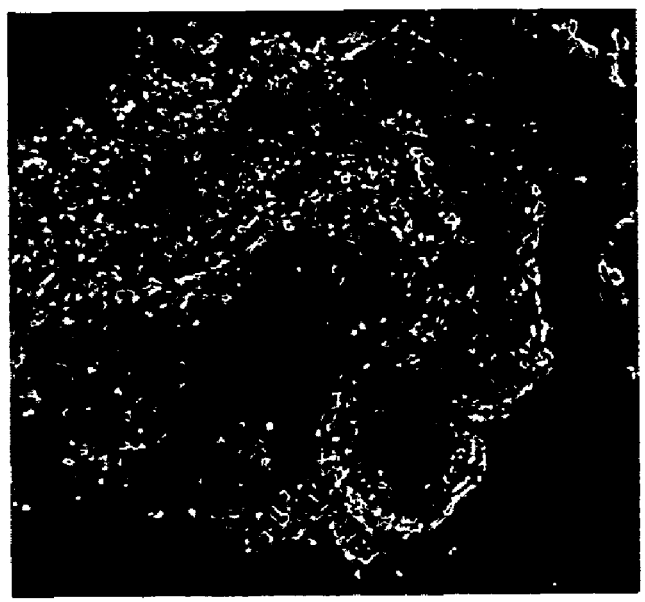

This marker is absent in other liver cells except in smooth muscle cells of large vessels, see Li et al. Hepatic Stellate Cells: Morphology, Function, and Regulation. In the Liver Biology and Pathology 4ed. 458 (2001) and Schmitt-Graff et al., Am J Pathol 138:1233-1242 (1991). The anatomical relationship of the α-SMA positive capsule and islet allografts were shown by multiple-color staining using anti-αSMA, anti-insulin and Hoescht (blue for nuclei). In the long-term euglycemic animals, functional islet allografts identified by positive insulin staining were encapsulated by multiple layers of αSMA positive cells (FIG. 3B). To ascertain the origin of these myofibrocytes—whether they were derived from transplanted I-1SCs or recruited from the host cells, BALB/c islet allografts were co-transplanted with fluorescent HSCs from EGFP mice (R6 background) (FIG. 3C) into B6 recipients. Animals were sacrificed on day 21 or 100 post-transplant with euglycemia. The grafts from day 21 animals showed that the fluorescent cells formed a multi-layered capsule (FIG. 3D). The long-term islet allografts (day 100) revealed healthy appearing islets with positive insulin staining that were surrounded by EGFP positive cells (FIG. 3E), indicating that the formed capsule is mainly originated from the co-transplanted HSCs.

Co-Transplantation with HSCs Attenuates T Cell Infiltration in Islet Grafts.

Figure 4A:
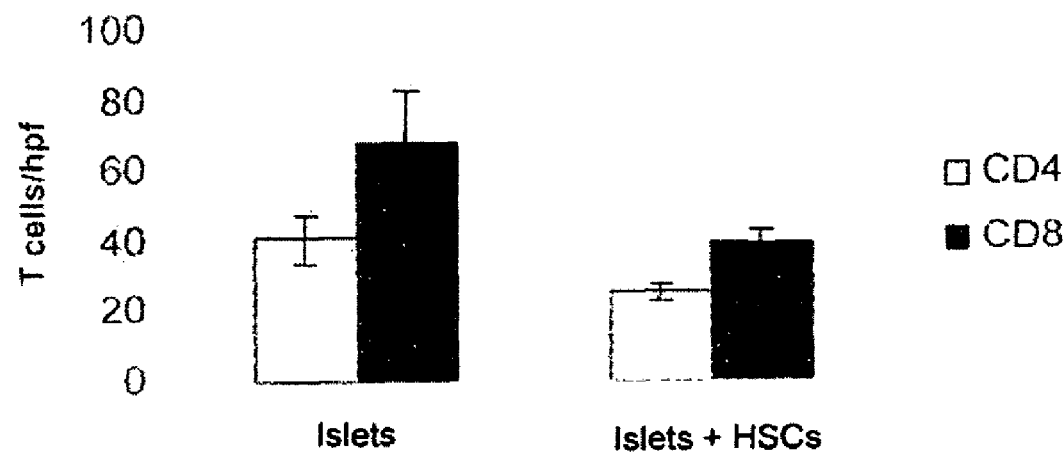
FIG. 4 illustrates acceptance of islet allografts by co-transplanted with HSCs is associated with decreased T cell infiltration and enhanced apoptotic activity. Chemically-induced diabetic B6 recipients were transplanted with 300 BALB/c islets alone or co-transplanted with same number BALB/c islets plus $3 \times 10^5$ B6 HSCs under left renal capsule (n=3 in each group). Animals were sacrificed on day 12 post-transplant. (A and B) The cryostat sections of the grafts were stained with biotinylated rat anti-CD4 or anti-CD8 mAb. The apoptotic cells were identified by TUNEL staining. The staining positive cells were counted under microscopy. A total of 30 high power fields (hpf) were randomly selected in each group. Data are expressed as mean positive cells per hpf±SD. (C) Graft sections were stained with fluorescent anti-insulin (green) and anti-αSMA (red, left panels) or anti-CD3 (red, right panels). The nuclei were stained with Hoescht (blue). In contrast to islet graft alone that showed scarred αSMA cells and heavy infiltration of CD3$^+$ T cells in the grafts, co-transplantation with HSCs demonstrated formation of multiple layers of αSMA cells surrounding the islets with much less infiltration of CD3$^+$ cells. These CD3$^+$ cells were trapped in the capsular layers composed of αSMA$^+$ cells.

The grafts from the recipients of islets allografts alone or islets allografts plus HSCs 12 days after transplantation were examined for graft T cell infiltration by immunohistochemical staining with anti-CD4 and -CD8 mAbs. Both CD4$^+$ and CD8$^+$ cells were significantly reduced in islet allografts co-transplanted with HSCs (FIG. 4A), indicating a role of HSCs in attenuating T cell infiltration. To illustrate the apoptotic activity, the grafts were examined by TUNEL staining. The apoptotic mononuclear cells were significantly increased in HSCs co-transplanted grafts (FIG. 4B), suggesting that induction of apoptotic death of infiltrating cells may be one of the underlying mechanisms. The anatomical relationship of infiltrated T cells and co-transplanted HSCs were demonstrated by the sequential sections and double stained with anti-insulin (green) and anti-αSMA or anti-CD3 (red). αSMA positive cells formed a capsule around the islets by day 12 and associated with light graft infiltration of CD3$^+$ cells. Most of the CD3$^+$ cells appeared to be trapped in the formed HSC capsules (FIG. 4C).

Effect of Co-Transplantation with HSCs on Revascularization in Islet Grafts.

Figure 5A:
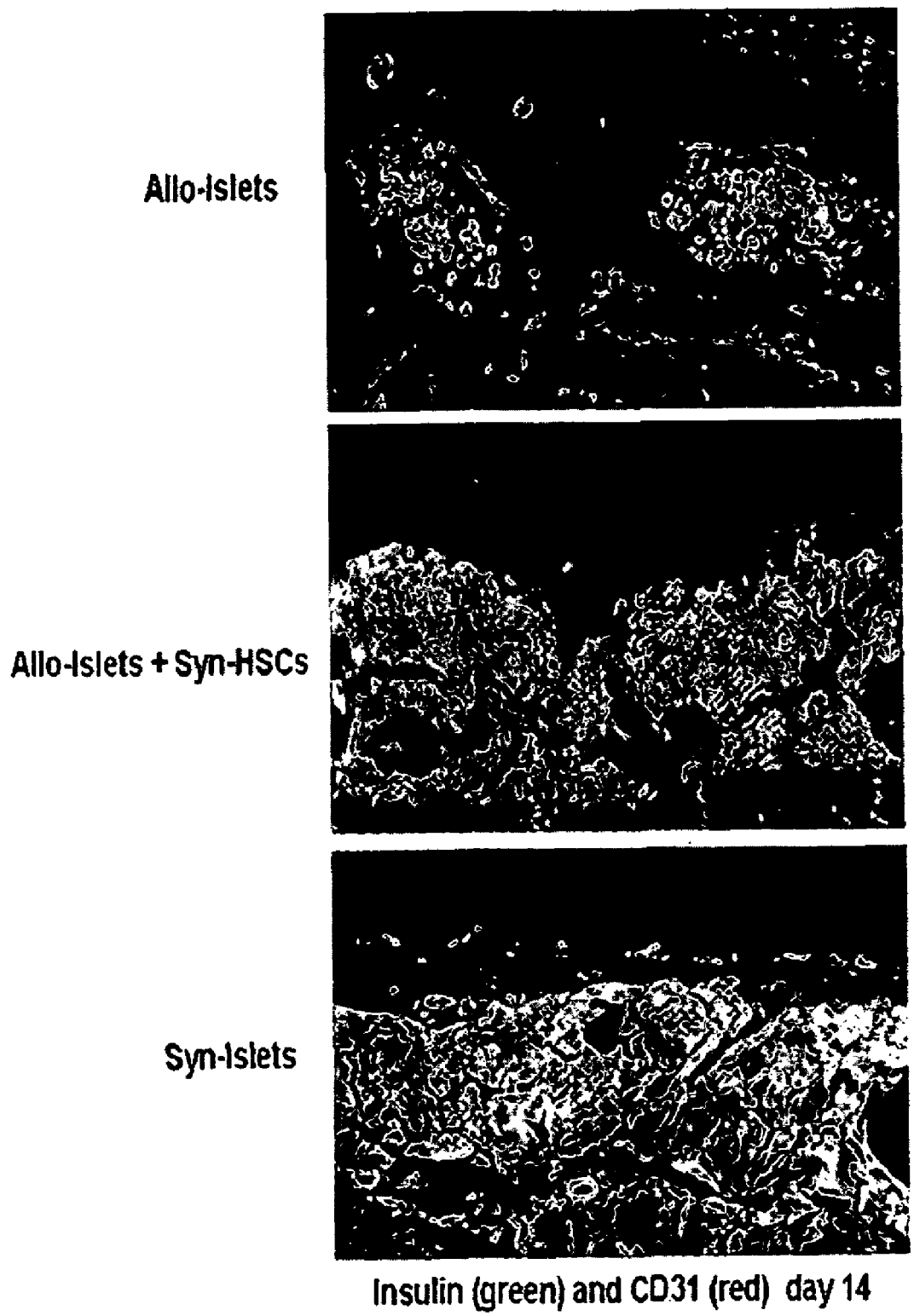
FIG. 5 illustrates co-transplant with HSCs enhances survival of islet allograft, but not vascularization. The islet grafts retrieved from B6 recipient diabetic mice 5 or 14 days after transplant of BALB/c (allogeneic) 300 islets alone or mixed with $3 \times 10^5$ B6 HSCs. Transplants of B6 islets alone were used as syngeneic controls (n=3 in each group). The sections were stained with anti-CD31 (red) and anti-insulin (green). (A) Histochemistry of islet grafts (14 days post-transplant). (B) Graft anti-CD31 immunostaining intensity. The relative intensity of immunostaining with anti-CD31 mAb within islet grafts was determined by computerized morphometric analysis. Anti-CD31 staining intensity in allo-islet plus HSCs group was significantly in higher than allografts alone group either on day 5 or 14 (both p<0.05), but was similar to that in syngeneic islets alone group (p>0.05). (C) Graft insulin content. The intensity of immunostaining with anti-insulin mAb within islet grafts was compared. The kidney transplanted with allo-islets plus HSCs displayed significantly higher insulin content than that transplanted with allo-islets alone (p<0.05).
Figure 5B:
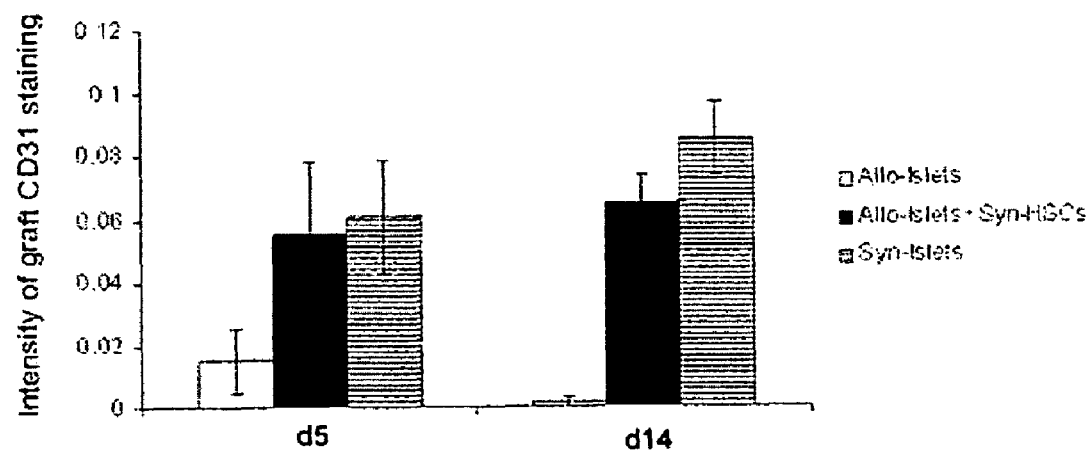
Figure 5C:
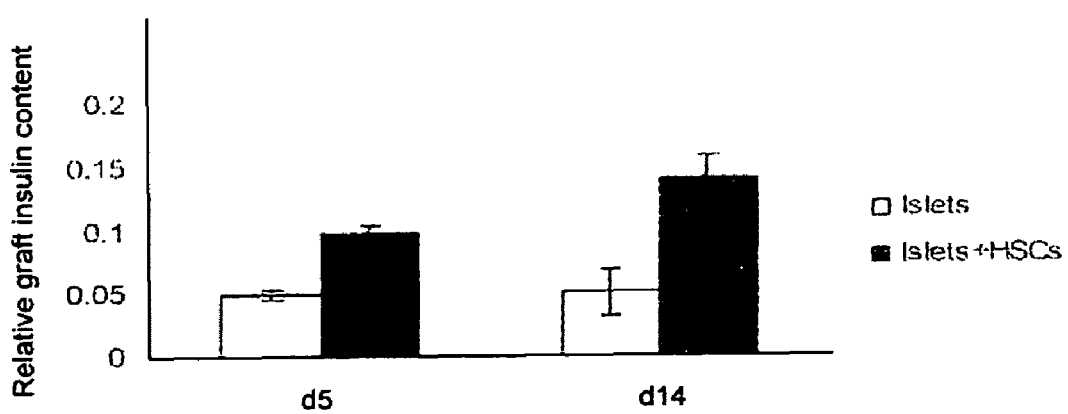

To evaluate the influence of co-transplanted HSCs on graft revascularization, the islet grafts were retrieved from the recipients that were sacrificed at 5 or 14 days post-transplant, and double stained with anti-CD31 (red) and anti-insulin (green). Islet grafts that were co-transplanted with HSCs exhibited more CD31$^+$ cells compared with islets alone group (FIG. 5A). CD31$^+$ cells were located at the edge of islet grafts in islets alone group, while, with co-transplantation of HSCs, many CD31 positive cells were seen within the islet grafts, reflecting a formation of vascular islands in the islet grafts (FIG. 5A). Quantification data indicated that the CD31 staining intensity in islet alone group was significantly lower than co-transplant group on day 5. By day 14 very few CD31 positive cells were detected in islet alone grafts, in contrast, revascularization in the grafts accompanied by HSCs was markedly enhanced (FIG. 5B, $p<0.05$ on day 5, $p<0.01$ on day 14). Consistent with the results of CD31 staining, the islets transplanted with HSCs displayed significantly higher insulin content than that islets alone (FIG. 5C, $p<0.05$). To determine whether the enhancement of CD31 expression was simply due to survival of islets or due to the presence of co-transplanted HSCs, syngeneic islets without HSCs were transplanted, and the grafts were stained with anti-CD31 for quantitative analysis. The data showing in FIG. 5B demonstrated that the average intensity of CD31 in syngeneic islets was less than allo-islet plus HSCs, but not statistically significant ($p>0.05$ both on day 5 and day 14), suggesting that the enhanced revascularization in islet allografts co-transplanted with HSCs is more likely related to survival of islet grafts than the presence of HSCs.

Involvement of B7-H1 in Immune Regulation Activity of HSCs.

Figure 6A:
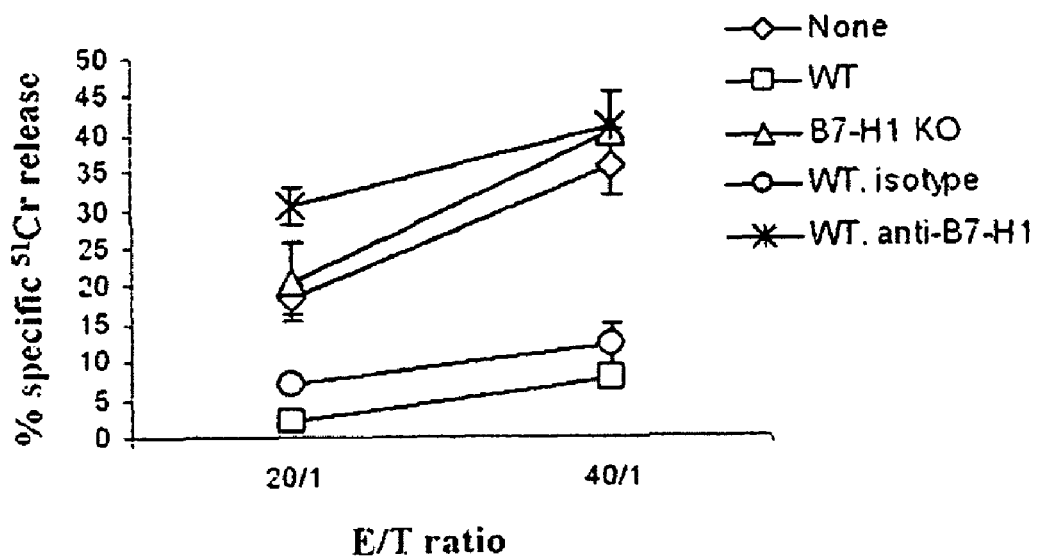
FIG. 6 illustrates a role of B7-H1 expressed on HSCs in inhibition of CTL generation. (A) B6 (H2$^b$) spleen T cells ($2 \times 10^5$) cultured with 7-irradiated (20Gy) BALB/c (H2$^d$) allogeneic DCs at a ratio of 10:1 for 5-6 days were used as effectors. To determine the effect of HSCs on T cell responses, γ-irradiated (50Gy) HSCs from wide type B6 (-□-), wide type B6 with anti-B7-H1 blocking mAb (15 μg/ml, rat IgG$_{2a}$, eBioscience, San Diego, Calif. [-X-] or isotype Ab [-O-]), or B6. B7-H1 KO (-Δ-) were added at HSC:T ratio of 1:40 at the beginning of the culture. P815 (H2$^d$), EL4 (H2$^b$), R1.1 (H2$^k$) or lymphoma cells labeled with 100 μCi Na$_2$$^{51}$CrO$_4$ (NEN, Boston, Mass.) were used as donor-specific, syngeneic or third party targets. They were plated in 96-well round-bottom and culture with effectors at E:T ratios of 40:1 and 20:1 in a total volume of 200 μl/well. CTL activity was examined in a 4 hour $^{51}$Cr release assay. No cytotoxicity was generated against syngeneic EL4 (H2$^b$) or third party R1.1 (H2$^k$) targets (data not shown). (B) Immunochemistry. Sections from islet allografts (B6) co-transplanted with B7H1$^{-/-}$ (became diabetic at day 26) or wild type HSCs (non-diabetic at day 65) were stained with anti-insulin (green) and anti-α-SMA (red). The nuclei were counter-stained by blue.

We have previously shown that quiescent HSCs (cultured for 2 days) expressed dim B7-H1, while expression of B7-H1 was markedly enhanced following in vitro activation, see Yu et al. (2004), indicating an inducible nature of B7-H1 expression on activated HSCs. In the present study, B6 B7-H1 KO mice were used. Deficiency in B7-H1 expression did not alter HSC proliferation and activation ability in culture compared with HSCs isolated from normal B6 mice determined by examination of cell yield number and expression of α-SMA. However, B7-H1 expression was crucial in their immune regulatory activity. In a 4 hour $^{51}$Cr release assay, the presence of wild type HSCs markedly suppressed generation of specific CTL activity against allogeneic targets, which was almost totally reversed by using B7-H-1$^{-/-}$ HSCs, or when function of B7-H1 was blocked by anti-B7-H1 mAb (FIG. 6). This was demonstrated in vivo by that co-transplantation of HSCs from B7-H1$^{-/-}$ livers largely lost their capacity to protect islet allografts from rejection (Table 1, $p<0.05$, group 8 vs. 3 $p>0.05$, group 8 vs. 1).

Figure 6B:
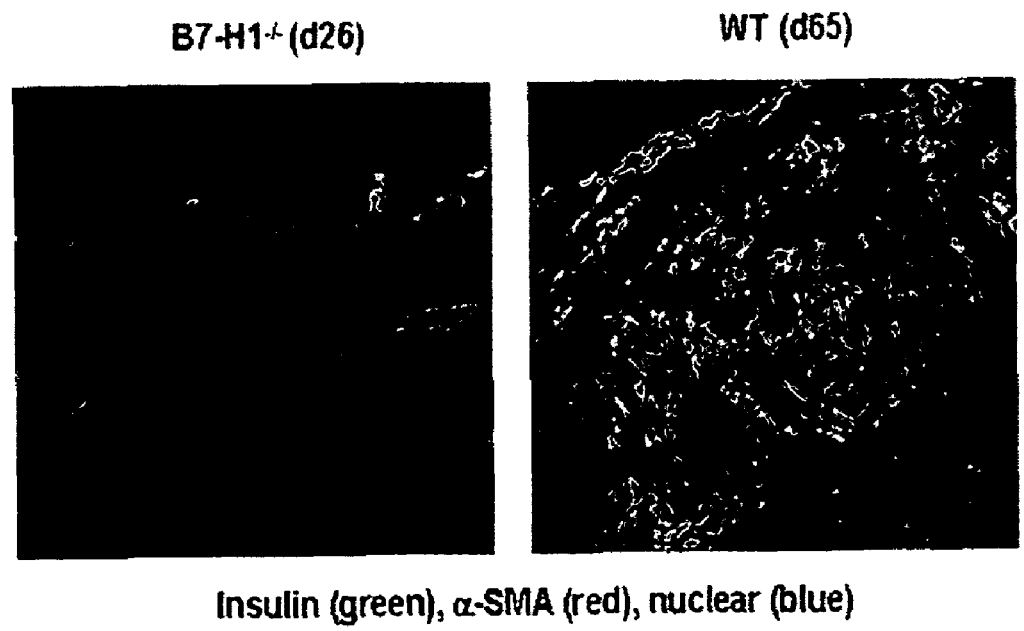

Immunochemical results demonstrated that islet allografts were rejected, but the co-transplanted B7-H-1$^{-/-}$ HSCs (syngeneic to recipients) appeared to survive when the animal became diabetic (FIG. 6B).

Discussion

We have recently demonstrated that activated HSCs suppress T cell responses in vitro by induction of activated T cell apoptosis, see Yu et al. (2004). The data in this study provide evidence of immune protective effect of activated HSCs in vivo. 55% of diabetic mice achieved long-term (>60 days) normoglycemia with transplantation of composite islet and activated HSC cellular grafts, whereas none of islet-only recipients remained normoglycemia more than 17 days. It is therefore, logically speculated that HSCs may play an important role in modulating immune responses in the liver, an immune privilege organ which was initially recognized by spontaneous acceptance of liver allografts, see Qian et al., Hepatology 19, 916-923 (1994). An immune privilege phenomenon has also been demonstrated in testis. Thus, islet allografts survived without immunosuppression, provided they were grafted into testis, see Whitmore et al. J Urol 134:782-786 (1985) and Selawry et al. Diabetes 33:405-406 (1984). Co-transplant with testicular Sertoli cells protected islet grafts from rejection similar to HSCs, see Selawry et al. (1984). However, the protective effect of HSCs appears to be more potent than Sertoli cells since the required cell number of HSCs ($3\times10^5$) was about 1/10 of Sertoli cells ($4-11\times10^6$), see Korbutt et al., Diabetologia 43:474-480 (2000) and Dufour et al., Transplantation 79: 1594-1596 (2003). Differences are also manifest by the local versus systemic effects. HSCs implanted distantly from islet allografts did not show protection. However, Sertoli cells protected the islets in the other side kidney, see Suarez et al., Diabetes 49:1810-1818 (2000). Moreover, co-transplanted HSCs need to be syngeneic (to the host) (Table 1), while allogeneic Sertoli cells prolonged survival of islet allografts, see Korbutt et al., Diabetes 46:317-322 (1997), suggesting involvement of different mechanisms. Thus, Sertoli cells may suppress immune response through Fas and/or TGF-β pathways, Suarez et al. (2000), by which the allogeneic Sertoli cells escape from host immune attack, while allogeneic HSCs may not be able to escape host immune attack. The results shown in Table 1 also indicate that, in contrast to activated HSCs (cultured for 7 days), co-transplant with quiescent HSCs (cultured for 2 days) showed no protective effect on survival of islet allografts. This is not surprising as quiescent HSCs express very few immune regulatory molecules, including B7-H1, TGF-β and IL-10 as shown in our previous study, see Yu et al, (2004).

Figure 4B:
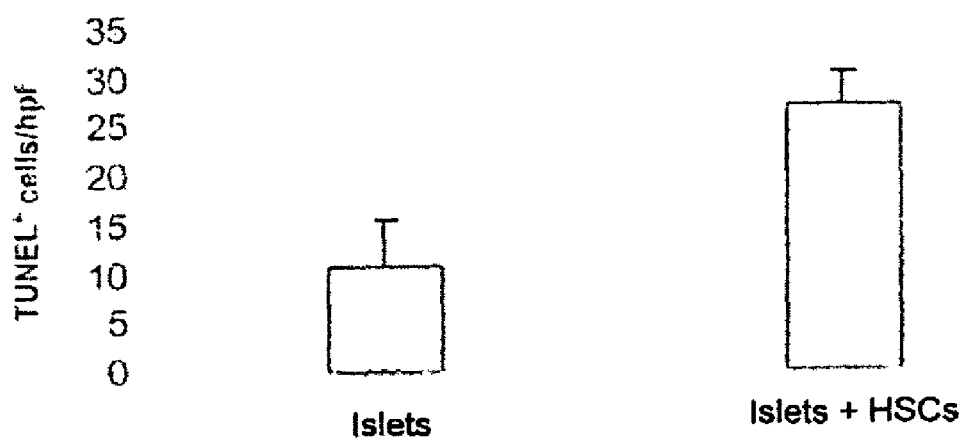

Although the exact mechanisms are not completely understood, our data showed a formation of capsules surrounding the islet allografts which was composed by multiple layers of α-SMA positive cells, and associated with significant reduction of grafts T cell infiltration. These α-SMA positive cells were shown origin of co-transplanted HSCs by using of EGFP mice. The reduction of infiltrating T cell number unlikely resulted from lacking of the chemotactie factors since activated HSCs produced numerous chemokines and attract leukocytes, see Friedman et al., J Biol Chem 275: 2247-2250 (2000) and Marra et al., J. Hepatol 31:1120-1130 (1999), rather was a result of enhanced apoptosis activity in infiltrated mononuclear cells (FIG. 4B). These findings are consistent with our previous observations. HSCs induced apoptotic death of activated T cells in vitro, see Yu et al. (2004). Formation of the protective capsules by co-transplanted HSCs may also explain why HSCs more effectively protect islet allografts than Sertoli cells which do not form the capsules. As well known, HSCs engage in capsulized fibrogenesis occurring in the injured or infected livers that distorts the normal hepatic architecture, see Bataller et al., Semin Liver Dis 21:437-51 (2001) and Rojkind et al., Pathology of liver fibrosis. In the Liver Biology and Pathology ($4^{th}$ Ed) 721 (2001). Treatment of liver fibrosis has been aimed to inhibit the accumulation of activated HSCs, see Bataller et al. (2001). However, the data of this study suggests that the liver fibrogenesis participated by HSCs may reflect a protective mechanism to avoid hepatocytes from overwhelming immunological injury. Therefore, the strategy of anti-fibrotic therapy needs to be cautiously re-evaluated in this light.

Our data suggest a critical role of induction of B7-H1 expression on HSCs in their immune regulatory effect. Quiescent HSCs do not express B7-H1, which is markedly upregulated following activation by various stimulators including IFN-γ and activated T cells; see Yu et al. (2004). This is consistent with other reports; B7-H1 is inducible in a variety of organs, including non-lymphoid tissues, see Dong et al., Nat Med 5:1365-1369 (1999). Our data show that HSCs deficient in B7-H1 lost the suppressive activity in inhibiting generation of specific CTL activity in vitro (FIG. 6), and HSCs isolated from B7-H1 KO mice failed to prolong survival of co-transplanted islet allografts (Table I). This may also explain the different effect of HSCs on naive and activated T cells. In contrast to their inhibitory effect on activated T cells, HSCs demonstrate modest stimulatory activity when culture with allogeneic T cells (Qian et al, unpublished data). This has also been shown in human HSCs, see Vinas et al., Hepatology 38: 919-929 (2003). B7-H1 ligation may contribute to inducing hyporesponsiveness of activated T cells via promoting their apoptotic death since the B7-H1 receptor PD-1 is inducibly expressed on activated T cells, see Chen et al., Blood 105:2242-2243 (2005). Other factors can not be excluded as blockade of B7-H1 ligation by mAb only partially reverses T cell inhibitory effect, and partially blocks the induction of T cell apoptosis, see Yu et al. (2004). B7-H1 has been shown to negatively regulate the immune system via down regulation at the effector phases. Ligation of PD-1, the receptor of B7-H1, and TCR leads to rapid phosphorylation of SHP-2, a phosphatase that attenuates TCR signaling which negatively regulates cytokine synthesis, see Dong et al., (1999), Freeman et al., J Exp Med 192: 1027-1034 (2000), Carter et al., Eur J Immunol 32:634-643 (2002), and Dong et al., Immunity 20:327-336 (2004). A recent study demonstrates that the deficiency of B7-H1 results in accumulation of $CD8^+$ T cells in the liver suggesting a role of B7-H1 in regulating T cell homeostasis, see Subudhi et al. Journal of Molecular Medicine 83:93-202 (2005). Therefore, B7-H1/PD-1 signaling pathway may play a critical role in maintaining peripheral tolerance. However, B7-H1 may not be the only molecule involved in the immunosuppressive activity of HSCs since blockage of B7-H1 ligation by addition of anti-B7-H1 mAb can only partially reverse the inhibition of T cell proliferation mediated by HSC in an MLR assay. Consistently, anti-B7-H1 mAb only partially reverses T cell apoptosis triggered by HSC, see Yu et al. (2004). Therefore, other pathways are expected to be involved. Thus, we have shown the expression of B7-H4 on activated HSC, see Yu et al., (2004). In addition, activated HSC also produce IL-10 and TGF-β, the cytokines with inhibitory and regulatory property in immune responses, which may provide synergizing signals with B7H1 in inhibition of immune responses.

While organ transplantation has been successful for decades, the outcome of cell transplantation remains disappointing. This is also true in animal models. Liver allografts are spontaneously accepted in many species, see Calne et al., Nature 233:472-474 (1969), Zimmerman et al., Transplant Proc 11:571-577 (1979), Kamada et al., Transplantation 29:429-431 (1980), and Qian et al., Hepatology 19:916-923 (1994) whereas hepatocyte allografis are promptly destroyed, succumbing to immune-mediated destruction since hepatocytes survive indefinitely in syngeneic recipients, as well as in allogeneic SCID mice, see Bumgardner et al., Immunological Reviews 175:260-279 (2000) and Bumgardner et al., Transplantation 65:53-61 (1998). The data demonstrated in this study suggest that the presence of NPC, such as HSCs, testicular Sertoli cells, etc. may attenuate immune attacks. Lacking of an appropriate tissue cell protection may relate to the poor outcome of cell transplants. This was hinted by previous clinical islet transplant studies. A significant positive correlation was observed between the number of ductal-epithelial cells and long-term islet allograft survival, see Street et al., Diabetes 53: 3107-3114 (2004). This was not due to the ductal cells containing islet progenitor cells, since β-cell renewal in adults did not originate from islet progenitors, see Sambanis, Diabetes Technol Ther 5:665-668 (2003).

To avoid immune attacks to islet transplants, an immunoisolation approach by encapsulation has been attempted using synthetic semipermeable membranes, see Lee et al., Adv Drug Delivery Reviews 42:103-120 (2000). They are however, not biocompatible, see Lee et al. (2000), and also cause insufficient oxygen and nutrient supplies, see de Vos et al. Diabetologia 45:159-173 (2002) and Zhang et al., Diabetes 53:963-970 (2004). Our results provide a hope to develop a biological encapsulation which are syngeneic and cause no biocompatibility problems. Activated HSCs produce hepatic growth factor (HGF), see Freidman, Nat Clin Prac Gastroenterology & Hepatology 1:98-105 (2004) which may favor islet cell proliferation, see Rao et al., Expert Opinion on Biological Therapy 4:507-518 (2004). A better understanding of the paradigm of local immunomodulation provided by HSCs may lead to development of novel strategies for cell transplantation and treatment of liver diseases.

EXAMPLE 2

In this study, we examined the immunoregulatory effect of HSC in vivo using an islet allograft transplantation model, and studied their effect on enhancing revascularization in islet grafts.

Materials and Methods

Animals

Male C57BL/6 (B6; $H2^b$) and BALB/c ($H2^d$) mice were purchased from Jackson Laboratory (Bar Harbor, Me.). All animals were maintained in the specific pathogen-free facility of Lerner Research Institute in Cleveland Clinic Foundation, provided with Purina Rodent Chow (Ralston Purina, St. Louis, Mo.) and tap water ad libitum for the duration of the experiment, and were used at 8-12 weeks of age.

Isolation and Culture of HSC

HSC were isolated from mouse livers as described. Briefly, the liver was perfused via the subhepatic vena cava with 20 mL Ca2+-Mg2+-free Hank's balanced salt solution (Mediatech, Herndon, Va.; 5 mL/min), followed by perfusion with 1 mL collagenase IV (1 mg/mL, Sigma, St. Louis, Mo.). The liver was removed, meshed, and agitated in collagenase IV (1 mg/mL) at 37° C. for 40 min. Cells were filtered through a nylon mesh and purified via Percoll (Sigma) gradient centrifugation. The isolated HSC were cultured ($10^5$/mL) in an uncoated plastic flask (Nunclon, Roskilde, Denmark) with RPMI-1640 (Mediatech) supplemented with 10% fetal calf serum and 10% horse serum in 5% CO2 in air at 37° C. for 1-2 weeks before use.

Islet Isolation and Transplantation

Mice were anesthetized with inhalation of isoflurane. The bile duct was identified and clamped at the papilla Vateri. Three to five milliliter of 1.5 mg/mL collagenase V solution was injected into the common bile duct leading to the pancreas. The pancreas was removed and incubated in a water bath at 37° C. for 30 min. After digestion, the suspension was washed two times in RPMI media and centrifuged for 1-2 min. Then pellets were resuspended in 10 mL histopaque (Sigma) and centrifuged for 20 min. The solution with islets was harvested and washed twice with RPMI media. Islets were sorted manually under a microscope. Three hundred purified islets alone or mixed with 3-5×$10^5$ HSC were aspirated into polyethylene tube (PE-50, Becton Dickinson, Parsippany, N.J.) and pelleted by centrifugation for 3 min.

Diabetes in mice was induced with a single intraperitoneal injection of streptozotocin (STZ) (220 mg/kg body weight, prepared in citrate buffer with pH 4.0; Sigma). Animals were monitored for blood glucose levels using a handheld glucometer (LifeScan, Mountain View, Calif.).

TABLE 2

Survival of Islet Allografts

| Cotransplant (day) | Islet survival (day) | MST (day) |
|---|---|---|
| None | 9 × 2, 10, 11 × 3, 12, 13, 14, 15 | 11 |
| HSC | 30, 35, 52,$^a$ 63,$^a$ 64,$^a$ 68,$^a$ 130 × 2$^a$ | 66 |

MST, median survival time.
$^a$All animals maintained euglycemia for more than 50 days post transplant, and were sacrificed on the indicated day for further studies.

Only mice with nonfasting blood glucose levels exceeding 350 mg/dL were used as recipients. Under anesthesia, an incision was made over the left kidney of the recipients. Three hundred islets with or without HSC were injected into subcapsular space. Transplantation was considered successful if the nonfasting blood glucose returned to normal (<200 mg/dL) in 2 days and lasted for the first 4 days post transplant. Glucose levels were measured 1-3 times a week post-transplant. Graft failure was defined as a rise in glucose levels over 350 mg/dL after a period of normoglycemia. No immunosuppressive reagents were administered throughout the experiments.

Immunochemical Staining

The kidney bearing the islet grafts was retrieved from recipient mice. Consecutive cryostat sections (5-6 μm thick) were cut and dried overnight at room temperature before immunostaining. The immunofluorescence protocols were performed to determine expression of CD31, and insulin using anti-CD31 (BD Pharmingen) and insulin mAbs (Santa Cruz Biotechnology, Santa Cruz, Calif.). Slides were analyzed using an Olympus BX 51 fluorescence microscope (Olympus America). Quantification of CD31 and insulin was performed using MetaMorph software.

Statistical Analysis

The parametric data were analyzed by Student's t test (2-tailed). Graft survival difference between groups of transplanted animals was compared using the Kaplan-Meier logrank test. A P value less than 0.05 was defined as significant.

Results

Protection of Islet Allografts by Cotransplantation with HSC

To determine the effect of cotransplantation with HSC on survival of islet allografts, 300 islets from BALB/c mice were mixed with 3×$10^5$ HSC from B6 livers, and transplanted under the renal capsule of B6 recipients. The data demonstrated in Table 1 showed that cotransplanted HSC markedly prolonged survival of islet allografts (P<0.01 compared with islet alone group). To confirm the function of islet allografts, all grafts survived for more than 50 days were removed by a nephrectomy at various time points as indicated in Table 2. The removal of islet allografts resulted in prompt recurrence of diabetes, suggesting that the transplanted islet grafts are responsible for maintaining euglycemia.

Figure 7:
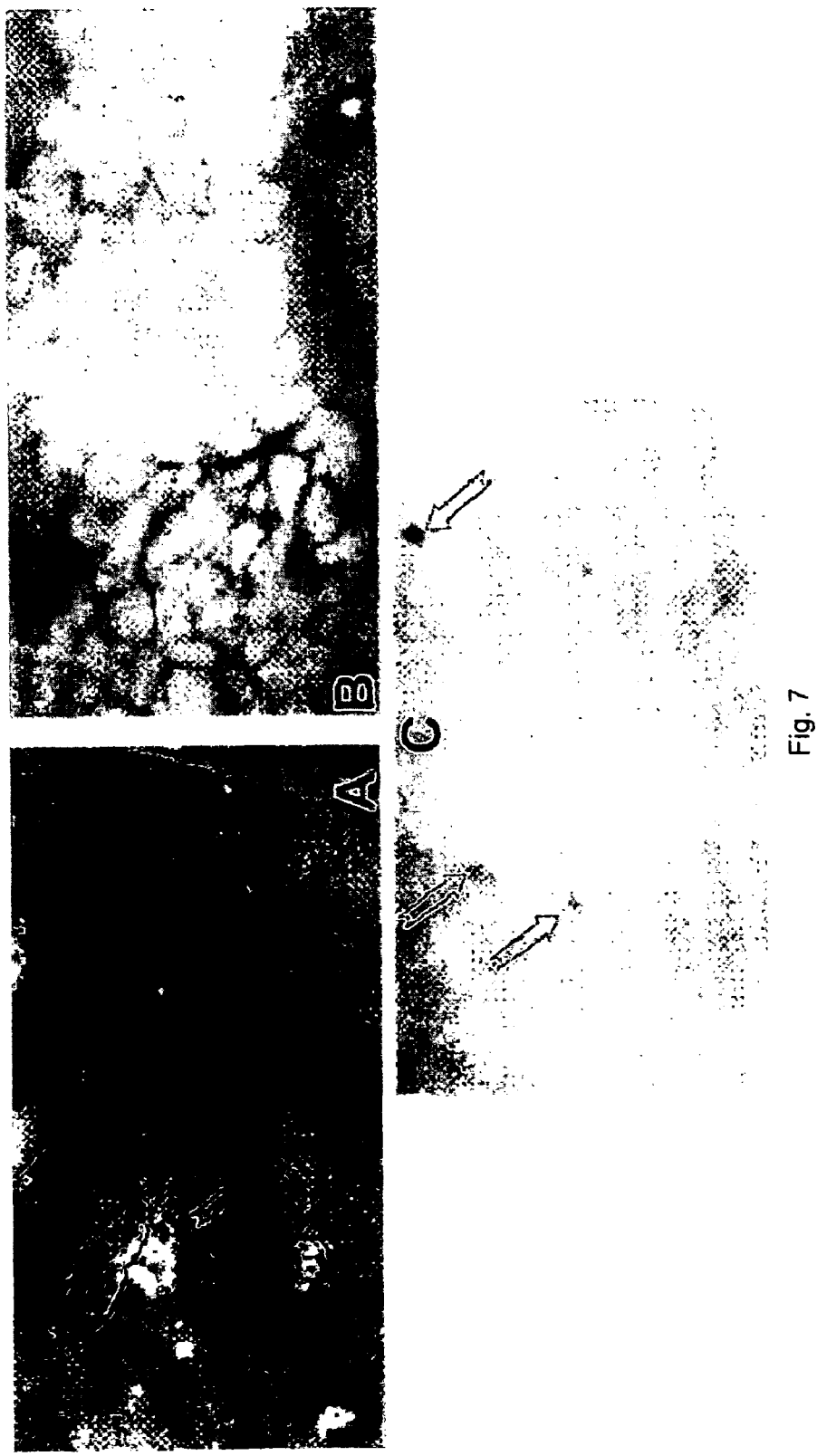
FIG. 7 are photographs illustrating revascularization in islet allografts cotransplanted with HSC. (A) The picture showed a BALB/c islet allograft was cotransplanted with B6 HSC (arrow) in a B6 recipient kidney 130 days post-transplant; (B) closer view of this islet graft showing abundant revascularization; (C) numerous vascular buds (arrows) were seen in an islet allograft that was cotransplanted with HSC 14 days post-transplant.
Figure 8:
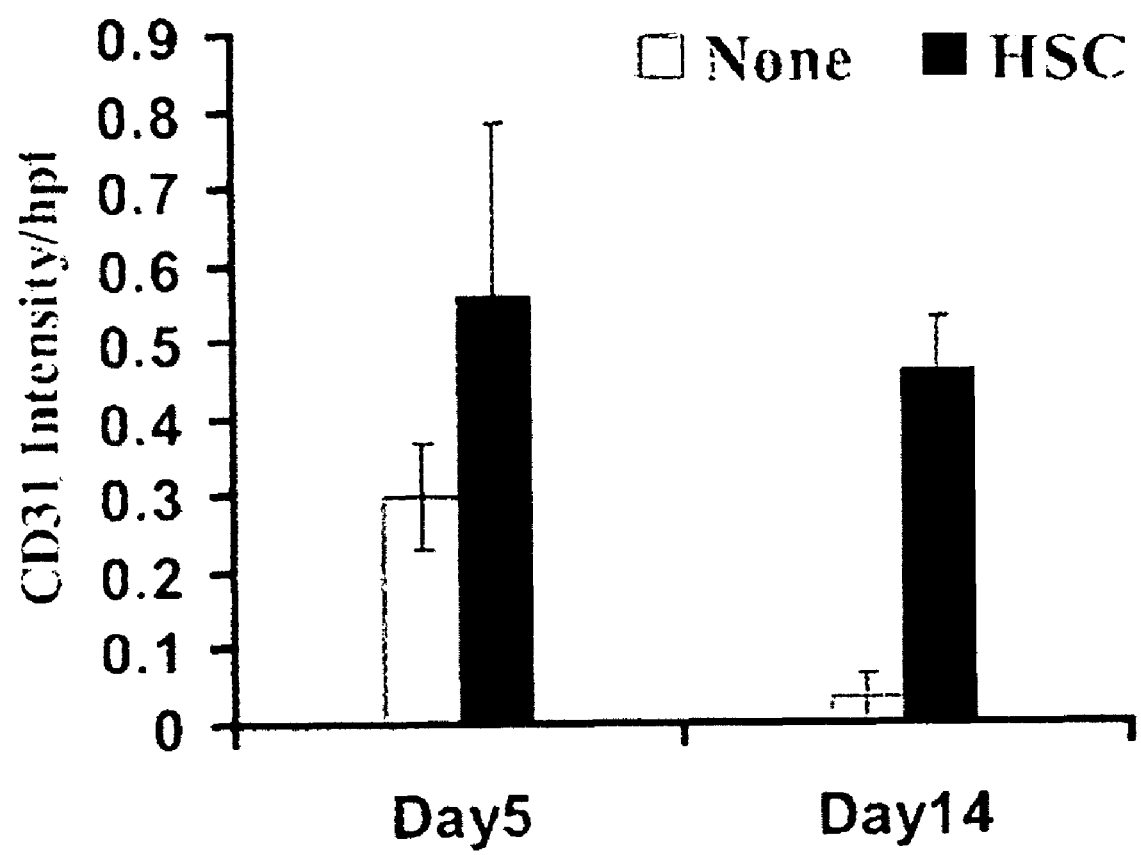
FIG. 8 is a graph illustrating cotransplant with HSC enhances vascularization in islet allografts. The islet grafts retrieved from B6 recipient diabetic mice 5 or 14 days after transplant of BALB/c islets alone or mixed with B6 HSC (n=3 in each group). The sections were double stained with anti-CD31 and anti-insulin. The intensity of immunostaining with anti-CD31 mAb within islet grafts was determined by computerized morphometric analysis. The data was expressed as CD31 intensity per high power field (hpf) of islet areas.

Survival of Islet Allografts is Associated with Enhancement of Revascularization Pictures in FIGS. 7A and 7B showed an islet allograft that were cotransplanted with HSC in a recipients maintaining normal blood glucose levels for 130 days post-transplant. That islet allograft contained abundant vasculatures. Indeed, the revascularization in islet allografts occurred as early as 14 days following cotransplantation with HSC, as shown in FIG. 7C. To ascertain the role of cotransplantation with HSC in enhancement of revascularization within islet allografts, the long-term survived grafts were double stained with anti-CD31 and anti-insulin. The islet grafts cotransplanted with HSC exhibited more CD31$^+$ cells compared with islets alone group either at day 5 or day 14 after transplant. CD31$^+$ cells were largely located at the edge of islet grafts in islets alone group, while with cotransplantation of HSC, many CD31$^+$ cells were seen within the islet grafts. Quantitative data showed that the CD31 staining intensity in islet alone group was significantly lower than in cotransplant group (FIG. 8, P<0.05 on day 5, P<0.01 on day 14), suggesting that the presence of HSC promote revascularization of islet allografts.

Discussion

In islet transplantation, which does not need vascular anastomosis in contrast to pancreas transplantation, neovascularization is considered to be an important process for the survival and function of the islets. It has been shown that microvascular perfusion to newly transplanted islets does not resume immediately after transplantation until 2 weeks before the reestablishment of a functional microvasculature in islet grafts. This was demonstrated in this study that cotransplant with HSC was associated with formation of vascular buds in islet allografts in 14 days post-transplant. A delay in islet revascularization may potentially deprive islets of oxygen and nutrients, resulting in islet cell death, particularly within the core of engrafted islets. This study also showed that islet allograft cotransplanted with HSC displayed a higher CD31 intensity than islet only group. CD31 is known not only as the earliest marker of endothelial cell differentiation but also as an angiogenic molecule playing a potential role in angioneogenesis. This finding strongly suggests that the presence of HSC favors the revascularization of islet allograft.

Because of the poor results of islet transplantation, an immunoisolation approach by encapsulation has been attempted, i.e., encapsulation with semipermeable membranes with pores of a size allowing passage of nutrients and metabolites but excluding large IgG molecules and lymphocytes. The materials currently used for encapsulation are synthetic, not completely biocompatible. In addition, islets within the membranes suffer from insufficient oxygen and nutrient supplies due to lack of revascularization. HSC provide a hope to develop a biological encapsulation technology which are syngeneic to the host and cause no biocompatibility problems and allow rapid revascularization, as demonstrated in this study. Indeed, activated HSCs secret vascular endothelial growth factor (VEGF) and hepatic growth factor (HGF). VEGF is an important angiogenic factor 18 and is critical for facilitating islet graft revascularization, while HGF favors islet cell proliferation.

From the above description of the invention, those skilled in the art will perceive improvements, changes and modifications. Such improvements, changes and modifications within the skill of the art are intended to be covered by the appended claims. All references, patents, and publications cited herein in this application are incorporated by reference in their entirety.

Having described the invention, the following is claimed:

1. A method of inhibiting islet graft rejection comprising:
isolating Hepatic Stellate Cells from a mammal liver;
activating the isolated Hepatic Stellate Cells;
mixing islet cells with the Hepatic Stellate Cells; and
administering the mixture of the islet cells and the activated Hepatic Stellate Cells to a mammal.

2. The method of claim 1 wherein the islet graft is selected from the group consisting of a xenograft, an allograft, and an autograft.

3. The method of claim 1 wherein the the mixture of the islet cells and the Hepatic Stellate cells comprise the islet cells pelleted with the Hepatic Stellate cells.

4. The method of claim 1, the Hepatic Stellate cells forming a multiple layered capsule surrounding the islet cells.

5. The method of claim 1 wherein the Hepatic Stellate cells form a coating surrounding the islet cells.

6. The method of claim 1 wherein the Hepatic Stellate cells are isolated from mammal liver non parenchymal cells.

7. The method of claim 1 wherein the isolated Hepatic Stellate cells are activated to express an immune regulatory molecule.

8. The method of claim 7 wherein the immune regulatory molecule comprises B7H1.

9. The method of claim 1 wherein the mixture of the islet cells and the activated Hepatic Stellate cells is administered to a mammal for the treatment of diabetes mellitus.

10. The method of claim 1 wherein the Hepatic Stellate cells are immunologically compatible to the mammal recipient.

* * * * *